(12) United States Patent
Dillard

(10) Patent No.: US 7,637,466 B2
(45) Date of Patent: Dec. 29, 2009

(54) UROLOGICAL INSTRUMENT MOUNTING DEVICE

(76) Inventor: Kaycell Dillard, 3907 Sadie Rd., Randallstown, MD (US) 21133

( * ) Notice: Subject to any disclaimer, the term of this patent is extended or adjusted under 35 U.S.C. 154(b) by 308 days.

(21) Appl. No.: 11/762,415

(22) Filed: Jun. 13, 2007

(65) Prior Publication Data
US 2008/0308688 A1 Dec. 18, 2008

(51) Int. Cl.
*E04G 3/00* (2006.01)

(52) U.S. Cl. .............. 248/280.11; 248/288.31; 248/288.51; 248/292.13; 403/149; 403/229

(58) Field of Classification Search .......... 248/274.1, 248/276.1, 280.11, 288.31, 288.51, 292.11, 248/292.13, 160, 158, 162.1, 371, 176.1, 248/181.1, 181.2, 183.1, 585, 586, 182.1; 403/149, 229, 56, 122
See application file for complete search history.

(56) References Cited

U.S. PATENT DOCUMENTS

| | | | | |
|---|---|---|---|---|
| 1,272,845 A * | 7/1918 | McClean | ............... | 248/586 |
| 1,460,697 A * | 7/1923 | Bendlin | ............... | 248/276.1 |
| 3,858,578 A | 1/1975 | Milo | | |
| 3,910,538 A * | 10/1975 | Baitella | ............... | 248/124.1 |
| 3,973,748 A * | 8/1976 | Nagasaka | ............... | 248/571 |
| 4,143,652 A | 3/1979 | Meier | | |
| 4,461,284 A | 7/1984 | Fackler | | |
| 4,573,452 A | 3/1986 | Greenberg | | |
| 4,606,522 A * | 8/1986 | Heifetz | ............... | 248/276.1 |
| 4,867,404 A | 9/1989 | Harrington | | |
| 5,224,680 A | 7/1993 | Greenstein | | |
| 5,284,130 A | 2/1994 | Ratliff | | |
| 5,447,149 A | 9/1995 | Kikiwada | | |
| 5,609,316 A * | 3/1997 | Tigliev | ............... | 248/123.11 |
| D389,913 S | 1/1998 | Bookwalter | | |
| 5,820,623 A | 10/1998 | Ng | | |
| 5,845,885 A * | 12/1998 | Carnevali | ............... | 248/181.1 |
| 5,876,325 A | 3/1999 | Mizuno | | |
| 5,899,425 A | 5/1999 | Corey, Jr. | | |
| 5,918,844 A | 7/1999 | Ognier | | |
| 6,085,749 A | 7/2000 | Wardle | | |
| 6,220,556 B1 * | 4/2001 | Sohrt et al. | ............... | 248/279.1 |
| 6,488,030 B1 | 12/2002 | Wardle | | |
| 6,550,734 B1 * | 4/2003 | Spadea | ............... | 248/280.11 |
| 6,639,789 B2 | 10/2003 | Beger | | |
| 6,834,837 B2 | 12/2004 | Schilt | | |
| 6,887,198 B2 | 5/2005 | Phillips | | |
| 6,952,986 B2 * | 10/2005 | Fu | ............... | 81/177.6 |
| 7,412,776 B2 * | 8/2008 | Iikubo et al. | ............... | 33/503 |
| 7,467,775 B2 * | 12/2008 | Lu et al. | ............... | 248/663 |

* cited by examiner

*Primary Examiner*—J. Allen Shriver
*Assistant Examiner*—Todd M. Epps
(74) *Attorney, Agent, or Firm*—Galbreath Law Offices, P.C.; John A. Galbreath

(57) ABSTRACT

A medical instrument mounting and positioning device is disclosed, comprising a platform with bilateral clamps to hold a camera or other instrument, said platform being movable via a swivel ball-and-socket joint and connected to a spring-tensioned articulated arm having a flexible coil and three longitudinal members connected by pivot screw joints. Another swivel ball joint is located at the non-instrument end of the articulated arm, to connect the arm to a support member that is anchorable to a surgical table or other surface.

17 Claims, 4 Drawing Sheets

UROLOGICAL INSTRUMENT MOUNTING DEVICE

FIELD OF THE INVENTION

The invention is in the area of medical instrument mounting and positioning devices.

DESCRIPTION OF THE RELATED ART

The prior art discloses various surgical instrument holders featuring articulated arms. However, none of these prior art devices exhibit the features of the present invention—that is, a platform with bilateral clamps to hold a camera or other instrument, said platform being rotatable via a swivel ball fitting and connected to a spring-tensioned articulated arm having a flexible coil, two additional pivot screw joints, and another swivel ball fitting. The invention's unique and innovative structure allows it to do a significantly better job of positioning surgical instruments in a flexible yet stable manner, thus freeing up the hands of surgeons and other medical personnel to perform other tasks.

U.S. Pat. No. 4,143,652 to Meier; U.S. Pat. No. 6,834,837 to Schilt; U.S. Pat. No. 6,639,789 to Beger; U.S. Pat. No. 4,461,284 to Fackler; U.S. Pat. Nos. 6,488,030 and 6,085,749, both to Wardle; U.S. Pat. No. 5,918,844 to Ognier; U.S. Pat. No. 5,224,680 to Greenstein; U.S. Pat. No. 5,820,623 to Ng; and U.S. Pat. No. 5,876,325 to Mizuno all disclose surgical instrument holders with arms that are articulated in various ways. However, none of these patents disclose a flat platform with two bilateral clamps attached to the working end of the arm, whereby a camera can be attached. In addition, these patents do not disclose a flexible lateral coil joint at the instrument mounting end of the arm, as in the device of the invention.

U.S. Pat. No. 6,887,198 to Phillips; U.S. Pat. No. 3,858,578 to Milo; U.S. Pat. No. 4,573,452 to Greenberg; U.S. Pat. No. 4,867,404 to Harrington; D389,913 to Bookwalter; U.S. Pat. No. 5,447,149 to Kikiwada; U.S. Pat. No. 5,284,130 to Ratliff; and U.S. Pat. No. 5,899,425 to Corey Jr. disclose devices that take a different approach to arm articulation. Instead of having relatively rigid arm segments that are connected by swivel, ball, or other joints to accomplish the articulation, these devices use continuously flexible lengths of tubing commonly referred to as "goosenecks". In some cases, the goosenecks are combined with one or more other joints in the articulated arm. Although the goosenecks in these devices resemble the flexible lateral coil joint in the invention, the physical structure of the rest of the arm (number of joints, type of joints, etc.) is markedly different from that of the invention. In addition, as with the prior art discussed above, none of these patents disclose a flat platform with two bilateral clamps attached to the working end of the arm, whereby a camera or other device can be attached. In addition to the above, two other patents—U.S. Pat. No. 6,220,556 to Sohrt and U.S. Pat. No. 3,910,538 to Baitella—disclose articulated arms that are used to hold things other than surgical instruments. However, these patents are not directed to surgical or urological instruments, and as a result, their physical structure is significantly different from that of the invention.

SUMMARY OF THE INVENTION

The invention is a medical instrument mounting and positioning device, comprising a platform with bilateral clamps to hold a camera or other instrument, said platform being movable via a swivel ball-and-socket joint and connected to a spring-tensioned articulated arm having a flexible coil, three longitudinal members connected by pivot screw joints, and another swivel ball joint connecting the articulated arm to a support member that is anchorable to a surgical table or other surface.

When performing various urological procedures, instrumentation is often used, and this can include cameras and other instruments. It is typically difficult for the surgeon to position and manipulate the instrument while also performing surgical techniques—sometimes the surgeon feels as if he or she needs four hands! Thus, there is a real need for a device that provides a stable, yet easily adjustable platform for a camera or other instrument during surgery.

Accordingly, several objects and advantages of the invention are:

It is an object of the invention to give the surgeon or other user increased instrument control and maximum flexibility, and free their hands to operate other devices and/or perform other surgical techniques.

It is a further object of the invention to provide the user with an enhanced ability to perform multiple tasks at the same time, in order to minimize both the time and personnel needed to perform surgical procedures.

It is a further object of the invention to provide a device that can be used effectively not only for urological procedures, but also for various other surgical and medical procedures.

Further objects and advantages of the invention will become apparent from a consideration of the ensuing description and drawings.

DETAILED DESCRIPTION OF THE INVENTION

Figure 1:
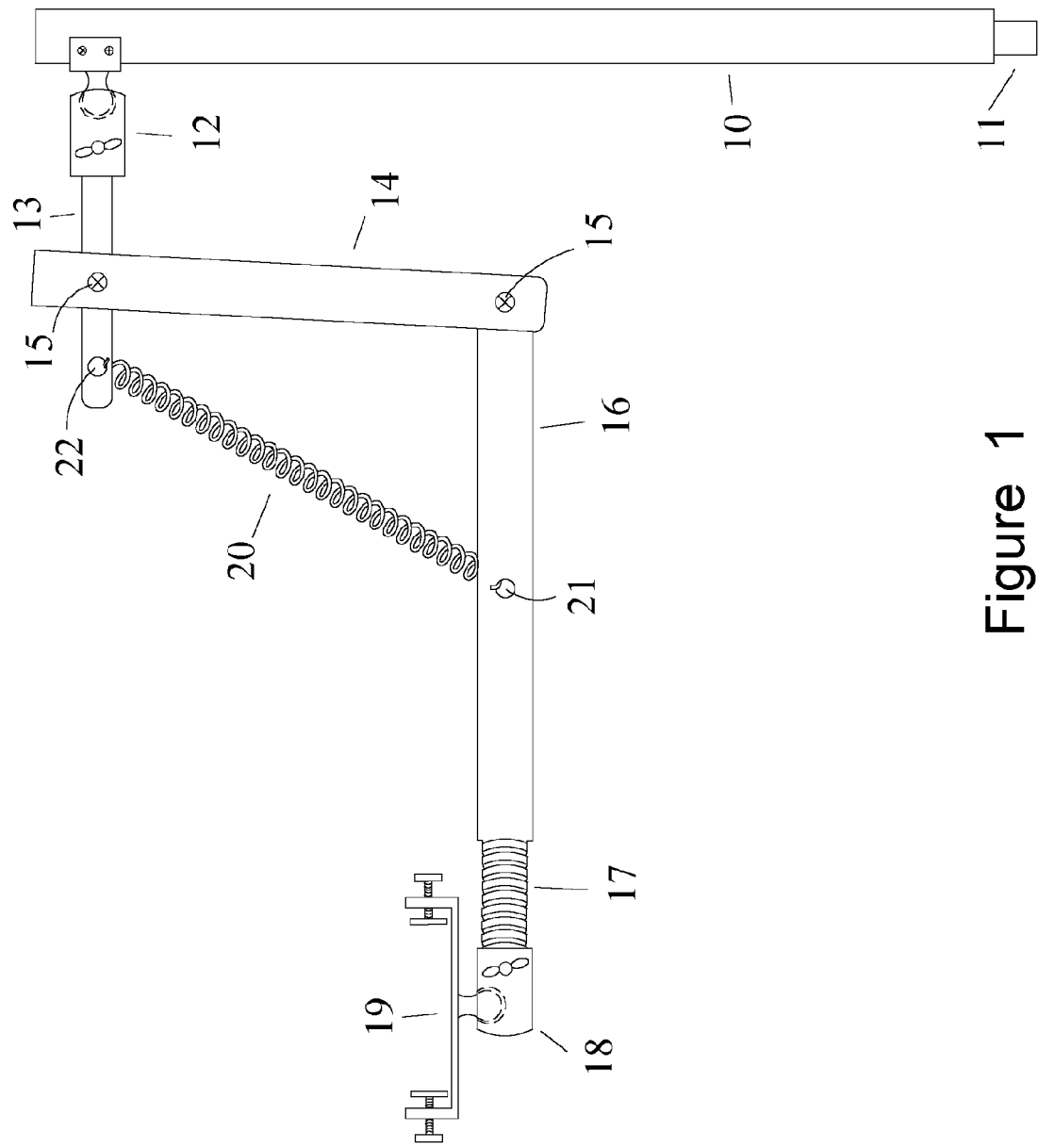
FIG. 1 illustrates the main structure of the device, comprising an assembly of members attached together via multiple articulating joints and having a platform at one end for holding a camera or other instrument.

The following provides a list of the reference characters used in the drawings:

| | |
|---|---|
| 10. | Support member |
| 11. | Anchor plug |
| 12. | Second hand-adjustable articulating joint |
| 13. | First articulating member |
| 14. | Second articulating member |
| 15. | Screw |
| 16. | Third articulating member |
| 17. | Flexible coil |
| 18. | First hand-adjustable articulating joint |
| 19. | Camera/instrument platform |
| 20. | Spring |
| 21. | First spring anchor hole |
| 22. | Second spring anchor hole |
| 23. | Floor |
| 24 a&b. | Side walls |
| 25. | Cord port |
| 26. | End wall |
| 27 a&b. | Thumbscrews |
| 28 a&b. | Bilateral holding plates |
| 29. | Bracket |
| 30. | Bracket attachment screw |
| 31. | Ball |
| 32. | Socket |

-continued

| | |
|---|---|
| 33 a&b. | Socket members |
| 34. | Handscrew |
| 35. | Video camera |

FIG. 1 illustrates the main structure of the inventive device. A support member 10, tubular in shape and substantially rigid, has an anchor plug 11 at its free end that is smaller in diameter than support member 10. This allows the free end of support 10 to be anchored in an operating table or other stable surface (not shown) by inserting anchor plug 11 into the operating table until support member 10 "grounds itself" onto the operating table surface.

A second hand-adjustable articulating joint 12 is attached to the other end of support member 10. This attachment can be made using screws or any other suitable method. The ball-and-socket structure of second hand-adjustable articulating joint 12 will be described further below, in the discussion of FIG. 4. The other end of second hand-adjustable articulating joint 12—that is, the end opposite the one attached to support member 10—is attached to a first articulating member 13. First articulating member 13 is also tubular in shape and substantially rigid, and is attached at a predetermined point along its length to a second articulating member 14, which is also tubular in shape and substantially rigid. The attachment between first articulating member 13 and second articulating member 14 is made by a screw 15 located transversely through the diameter of these two members, and the attachment is such that these two members can rotate relative to one another in the plane perpendicular to the direction of screw 15. The user can set screw 15 loosely, so that the two members rotate freely, or the user can tighten screw 15 so that the two members are locked together in a desired position.

The other end of second articulating member 14 is attached to a third articulating member 16, which is also tubular in shape and substantially rigid. The attachment between second articulating member 14 and third articulating member 16 is similar to the attachment between first articulating member 13 and second articulating member 14, and is also made by a screw 15 located transversely through the diameter of these two members. The attachment is such that these two members can rotate relative to one another in the plane perpendicular to the direction of screw 15. The user can set screw 15 loosely, so that the two members rotate freely, or the user can tighten screw 15 so that the two members are locked together in a desired position.

A flexible coil 17 is located at the other end of third articulating member 16. Flexible coil 17 is similar in structure to various "gooseneck" components that are known in the art, i.e., it allows the position of items connected to it to be changed, and then the new position is held until a further change in position is desired. Thus, flexible coil 17 provides additional instrument positioning capability. The other end of flexible coil 17 is attached to first hand-adjustable articulating joint 18, which has a ball-and-socket structure similar to that of second hand-adjustable articulating joint 12 except that the opening to the socket is located at the side (along the length) of first hand-adjustable articulating joint 18, instead of at the end as in second hand-adjustable articulating joint 12. The ball component thus extends substantially vertically from the socket of first hand-adjustable articulating joint 18, and is attached at its other end to camera/instrument platform 19. Thus camera/instrument platform 19 can swivel and rotate relative to first hand-adjustable articulating joint 18, in the manner consistent with ball-and-socket joints. The specific structure of camera/instrument platform 19 will be described further below, in the discussion of FIG. 2.

A spring 20 stretches between a first spring anchor hole 21, which is located at a predetermined point along the length of third articulating member 16, and a second spring anchor hole 22, which is located at a predetermined point along the length of first articulating member 13, beyond the point at which first articulating member 13 is attached to second articulating member 14. It can be understood that the tension of spring 20 serves to balance the weight of the camera or other instrument which is mounted in camera/instrument platform 19 and keep the vertical position of camera/instrument platform 19 at a desired point.

Figure 2:
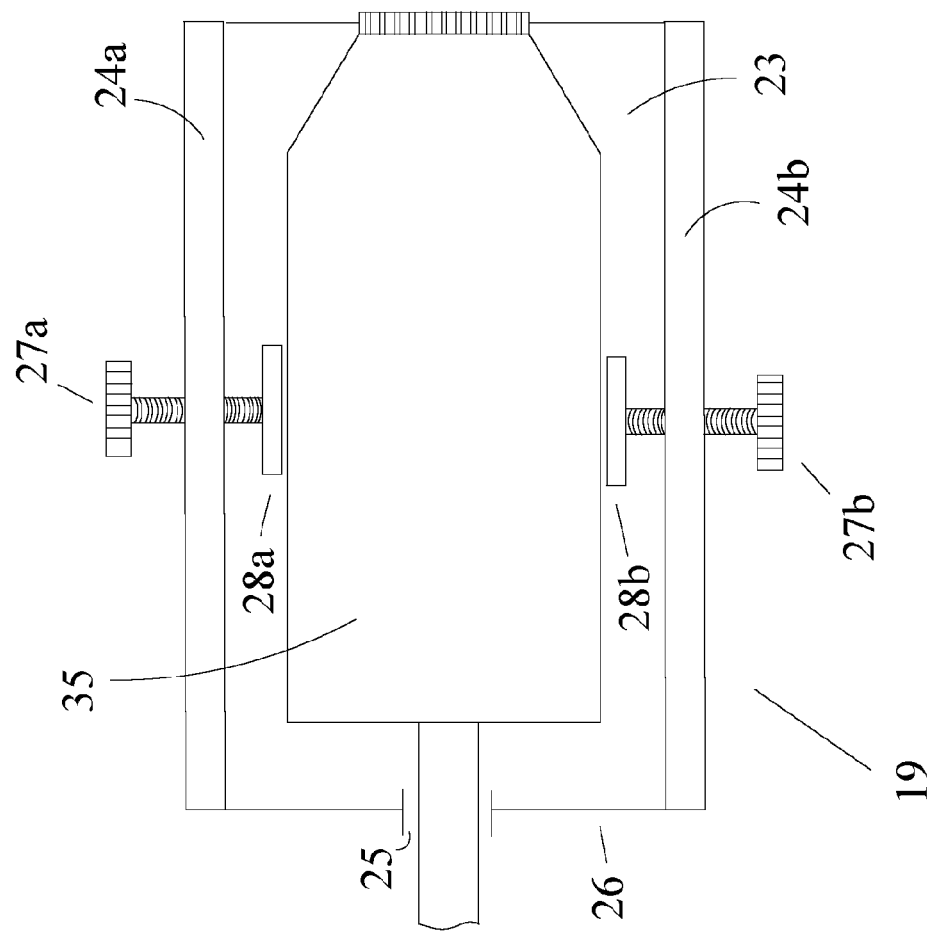
FIG. 2 is a detailed top view of the camera/instrument platform.

Turning now to FIG. 2, which shows camera/instrument platform 19 in detail, the platform comprises a substantially flat floor 23 and two opposing side walls 24a&b which extend from floor 23 and run along its length. By way of non-limiting example, FIG. 2 shows a video camera 35 positioned within camera/instrument platform 19. Camera/instrument platform 19 has no front wall, such that the camera or other instrument can be "pointed" out the front end of the platform. A cord port 25, or opening, is located in an end wall 26 of camera/instrument platform 19, such that a power cord, data transmission cable, or other component can extend from the camera or other instrument out through end wall 26.

Thumbscrews 27a&b are located through side walls 24a&b respectively, and are attached at their platform-interior ends to bilateral holding plates 28a&b respectively. Bilateral holding plates 28a&b serve to clamp the camera or other instrument that is placed in camera/instrument platform 19, so that it is securely held in position. It can be appreciated that thumbscrews 27a&b can be turned in or out to adjust the position of bilateral holding plates 28a&b and thus clamp objects of varying size and shape.

Figure 3:
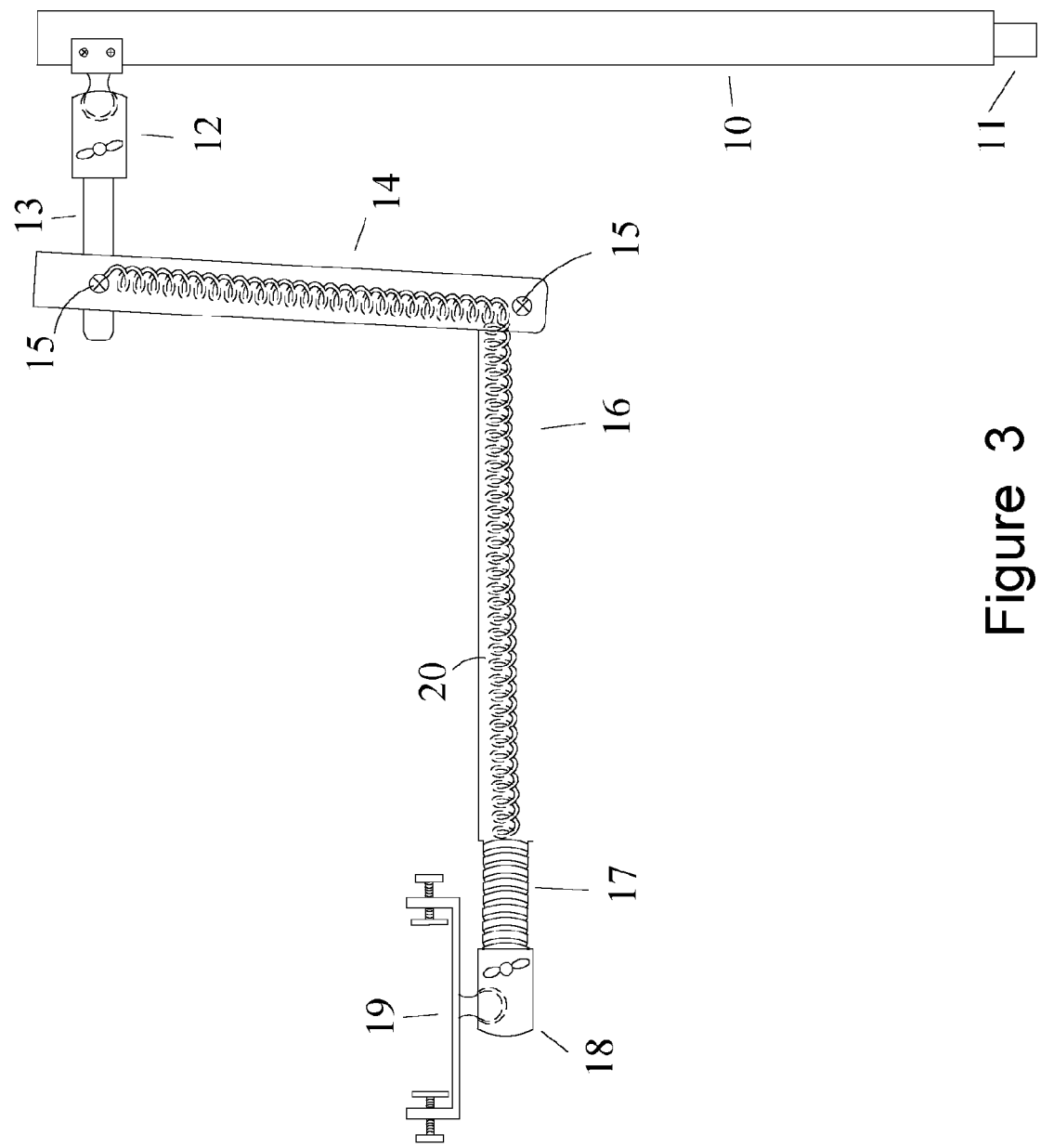
FIG. 3 illustrates an alternative embodiment, wherein the spring that tensions two of the articulating members is located within the interior of those members.

FIG. 3 illustrates an alternative embodiment, wherein spring 20 is located within the interior of second articulating member 14 and third articulating member 16. In this alternative embodiment, spring 20 tensions these two members from the inside, rather than from the outside as in the main embodiment.

Figure 4:
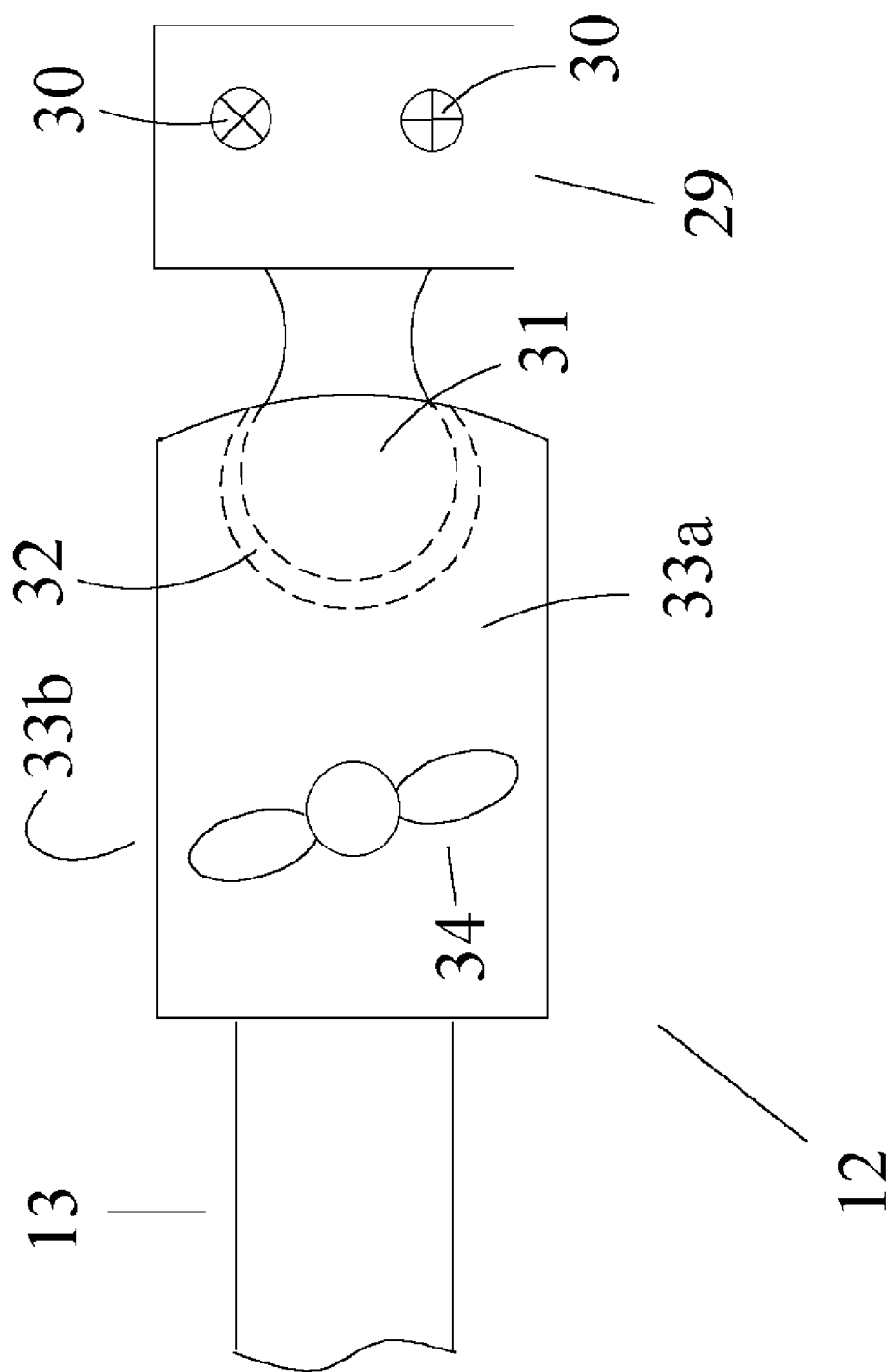
FIG. 4 is a detailed view of the hand-adjustable articulating joint.

Turning now to FIG. 4, which shows second hand-adjustable articulating joint 12 in detail, the joint comprises a bracket 29 having a plurality of through-holes containing screws 30, by which bracket 29 is attached to support member 10. Ball 31 is attached to bracket 29. Ball 31 rests inside socket 32, which is formed by two corresponding socket members 33a&b having generally hemispherical hollows located on their corresponding sides. These generally hemispherical hollows form socket 32 when the corresponding sides of sockets members 33a&b are put together.

A handscrew 34 extends through socket member 33a and into socket member 33b, thus connecting sockets members 33a&b together. Ball 31 can swivel and rotate relative to socket 32, thus allowing the position of the articulating members to be adjusted relative to support member 10. The user can loosen handscrew 34, adjust the device to the desired position, and then tighten handscrew 34 to clamp ball 31 securely within socket 32 and hold the desired position.

First hand-adjustable articulating joint 18 is constructed similarly to second hand-adjustable articulating joint 12, except that the ball is attached to camera/instrument platform 19 instead of bracket 29. In addition, as discussed earlier, the opening to the socket is located at the side (along the length) of first hand-adjustable articulating joint 18, instead of at the end as in second hand-adjustable articulating joint 12.

It should be understood that in second hand-adjustable articulating joint 12, and indeed in first hand-adjustable articulating joint 18, the two socket members that form the socket also serve to clamp first articulating member 13 and flexible coil 17 respectively, when the socket members are pressed together by handscrew 34. Alternatively, second hand-adjustable articulating joint 12 and first hand-adjustable articulating joint 18 can be constructed such that their non-socket ends are attached to first articulating member 13 and flexible coil 17 by other means, with handscrew 34 serving only to clamp the ball within the socket. In such an embodiment, the socket portion of the articulating joint would be formed of one solid part, with a "split" extending along part of its length. The split allows the socket ends to move independently enough of one another so that their proximity, and thus the clamping action on the ball, could be adjusted with the handscrew.

To use the device, the anchor plug 11 end of support member 10 is inserted into a suitably-sized opening in an operating table or other surface. A camera or other instrument is placed in camera/instrument platform 19, and secured in place using thumbscrews 27*a*&*b*. Handscrews 34 on second hand-adjustable articulating joint 12 and first hand-adjustable articulating joint 18 are loosened sufficiently to allow the assembly to be positioned as desired, and then handscrews 34 are tightened to lock the assembly, and thus the camera or other instrument, in the desired position. Subsequent changes in position are accomplished in a similar manner.

An alternative mode of operation is also envisioned, wherein via one or both handscrews, the user sets the "drag" so that the ball will hold its position within the socket against gravity, yet still be movable when a certain amount of force is applied by the user. In such a mode, the instrument position will be adjustable if sufficient force is applied, yet still be stable in the absence of user-applied force.

While the above descriptions contain many specificities, these shall not be construed as limitations on the scope of the invention, but rather as exemplifications of embodiments thereof. Many other variations are possible without departing from the spirit of the invention. Examples of just a few of the possible variations follow:

Different attachment means can be used to attach the inventive device to the surgical table or other surface. By way of non-limiting example, a clamp can be used instead of the anchor plug shown and described.

The support member and/or articulating members can be made from other than tubular stock—by way of non-limiting example, flat bar stock or square box stock can be used.

The dimensions (length, width, diameter, etc.) of the components in the device—the support member, the articulating members, and other components—can vary.

Joint structures can be used that are different than those shown and described. By way of non-limiting example, hand-adjustable joints can be substituted for non-hand adjustable joints (i.e., joints that are adjusted using a tool), and vice-versa.

The tension of the spring can be adjusted either by using springs with different Hooke's constants (also known as spring constants or force constants), by having several differently-located spring anchor holes in the articulating members, or by having spring mounting means at one or both spring ends that can slide along the length of the articulating member and then be fixed in a desired position, so as to increase or decrease the spring tension.

An elastic band or other tensioning device can be used instead of the coil spring shown and described.

Accordingly, the scope of the invention should be determined not by the embodiments illustrated, but by the appended claims and their legal equivalents.

What is claimed is:

1. A medical instrument mounting device, comprising:
   (a) a support member having means for engaging a stable surface;
   (b) an articulated arm attached to the support member;
   (c) a flexible coil attached to the articulated arm;
   (d) a first swivel ball joint attached to the flexible coil; and
   (e) an instrument platform attached to the first swivel ball joint;
   whereby an instrument can be mounted on the instrument platform and positioned in a desired orientation.

2. The device of claim 1, wherein said articulated arm comprises a first articulated member attached to said support member, a second articulated member pivotably attached to the first articulated member, and a third articulated member pivotably attached to the second articulated member.

3. The device of claim 2, wherein said device also comprises means for tensioning the second and third articulating members.

4. The device of claim 3, wherein said tensioning means is an externally-mounted spring.

5. The device of claim 3, wherein said tensioning means is a spring located within the second and third articulating members.

6. The device of claim 1, wherein said instrument platform includes securing means to hold an instrument.

7. The device of claim 6, wherein said securing means comprise bilateral clamps to hold an opposing sides of an instrument.

8. The device of claim 1, wherein said device also comprises a second swivel ball joint located between the articulated arm and the support member.

9. The device of claim 1, wherein said engaging means is an anchor plug.

10. A medical instrument mounting device, comprising:
    (a) a support member having means for engaging a stable surface;
    (b) a first articulated member attached to said support member;
    (c) a second articulated member pivotably attached to the first articulated member;
    (d) a third articulated member pivotably attached to the second articulated member;
    (e) a first swivel ball joint attached to the third articulated member;
    (g) an instrument platform attached to the first swivel ball joint;
    whereby an instrument can be mounted on the instrument platform and positioned in a desired orientation.

11. The device of claim 10, wherein said device also comprises means for tensioning the second and third articulating members.

12. The device of claim 11, wherein said tensioning means is an externally-mounted spring.

13. The device of claim 11, wherein said tensioning means is a spring located within the second and third articulating members.

14. The device of claim 10, wherein said instrument platform includes securing means to hold an instrument.

15. The device of claim 14, wherein said securing means comprise bilateral clamps to hold an opposing sides of an instrument.

16. The device of claim 10, wherein said device also comprises a second swivel ball joint located between the first articulated member and the support member.

17. The device of claim 10, wherein said engaging means is an anchor plug.

* * * * *